US011124438B2

(12) United States Patent
Xue et al.

(10) Patent No.: US 11,124,438 B2
(45) Date of Patent: Sep. 21, 2021

(54) ALCALIGENES FAECALIS FOR DEGRADING ETHYLENE OXIDE

(71) Applicants: Chio Kang Medical, Inc., Palo Alto, CA (US); QIAOKANG BIOTECH (GUANGDONG) CO., LTD., Guangzhou (CN)

(72) Inventors: Jianlong Xue, Guangzhou (CN); Dongxin Hou, Guangzhou (CN); Lijuan Jiang, Guangzhou (CN); Weiguo Wang, Guangzhou (CN); Xuzhong Liao, Guangzhou (CN); Yecheng He, Guangzhou (CN); Hao Chen, Guangzhou (CN); Jiali Lin, Guangzhou (CN); Ziping Zhu, Guangzhou (CN); Lixiong Feng, Guangzhou (CN)

(73) Assignees: CHIO KANG MEDICAL, INC., Palo Alto, CA (US); QIAOKANG BIOTECH (GUANGDONG) CO., LTD., Guangdong (CN)

( * ) Notice: Subject to any disclaimer, the term of this patent is extended or adjusted under 35 U.S.C. 154(b) by 0 days.

(21) Appl. No.: 17/012,843

(22) Filed: Sep. 4, 2020

(65) Prior Publication Data
US 2021/0221718 A1 Jul. 22, 2021

Related U.S. Application Data

(63) Continuation of application No. PCT/CN2020/101139, filed on Jul. 9, 2020.

(30) Foreign Application Priority Data

Jan. 20, 2020 (CN) .......................... 202010064633.4
Jan. 20, 2020 (CN) .......................... 202010064718.2

(51) Int. Cl.
*C02F 3/34* (2006.01)
*C12N 1/20* (2006.01)
(Continued)

(52) U.S. Cl.
CPC .................. *C02F 3/34* (2013.01); *C02F 3/28* (2013.01); *C12N 1/20* (2013.01); *C12N 1/205* (2021.05);
(Continued)

(58) Field of Classification Search
CPC .......... C02F 3/34; C02F 3/28; C02F 2101/34; C02F 2103/18; C12N 1/20; C12R 1/05
(Continued)

(56) References Cited

U.S. PATENT DOCUMENTS 1,954,056 A 4/1934 Miller
2,586,670 A 2/1952 Lambertsen
(Continued)

FOREIGN PATENT DOCUMENTS

CN 1223166 A 7/1999
CN 1397474 A 2/2003
(Continued)

OTHER PUBLICATIONS

CN106754585 Yongsheng et al.—*Alcaligenes faecalis* YS302 and applications thereof (Abstract & MT; May 31, 2017). (Year: 2017).*
(Continued)

*Primary Examiner* — Hayden Brewster
(74) *Attorney, Agent, or Firm* — Adsero IP

(57) ABSTRACT

The present disclosure provides an *Alcaligenes faecalis* strain capable of degrading ethylene oxide and uses thereof. The deposit number of the strain is CGMCC No. 18435. This strain can be used in pollution treatment, for example, to treat industrial sewage or wastewater containing ethylene oxide, which greatly improves the decontamination ability
(Continued)

of ethylene oxide in manufacturing industries. The present disclosure also provides a degradation agent for degrading ethylene oxide and a method for biodegrading ethylene oxide.

9 Claims, 3 Drawing Sheets

Specification includes a Sequence Listing.

(51) Int. Cl.
   *C02F 3/28*      (2006.01)
   *C02F 101/34*    (2006.01)
   *C12R 1/05*      (2006.01)
   *C02F 103/18*    (2006.01)

(52) U.S. Cl.
   CPC ...... C02F 2101/34 (2013.01); C02F 2103/18 (2013.01); C12R 2001/05 (2021.05)

(58) Field of Classification Search
   USPC .................................. 210/601, 605, 630
   See application file for complete search history.

(56) References Cited

U.S. PATENT DOCUMENTS

| | | | |
|---|---|---|---|
| 2,817,689 A | 12/1957 | White | |
| 3,022,054 A | 2/1962 | Kotzebue | |
| 3,572,391 A | 3/1971 | Hirsch et al. | |
| 3,598,543 A | 8/1971 | Crosby et al. | |
| 3,844,739 A | 10/1974 | Alfrey, Jr. | |
| 3,961,920 A | 6/1976 | Gilbert | |
| 3,997,633 A | 12/1976 | Leva et al. | |
| 4,112,054 A | 9/1978 | Feingold et al. | |
| 4,119,539 A | 10/1978 | Ettel et al. | |
| 4,134,425 A | 1/1979 | Gussefeld et al. | |
| 4,243,636 A | 1/1981 | Shiraki et al. | |
| 4,274,954 A | 6/1981 | Blair | |
| 4,301,113 A | 11/1981 | Alguire et al. | |
| 4,517,167 A | 5/1985 | Popescu et al. | |
| 4,549,363 A | 10/1985 | Buonicore | |
| 4,831,196 A | 5/1989 | Buonicore et al. | |
| 5,084,075 A | 1/1992 | Sircar | |
| 5,204,075 A | 4/1993 | Jain et al. | |
| 5,270,000 A | 12/1993 | Goldner et al. | |
| 5,283,035 A | 2/1994 | Karthaus et al. | |
| 5,290,345 A | 3/1994 | Osendorf et al. | |
| 5,511,409 A | 4/1996 | Knaebel | |
| 5,522,808 A | 6/1996 | Skalla | |
| 5,607,652 A | 3/1997 | Hellmuth et al. | |
| 5,641,455 A | 6/1997 | Rosenlund et al. | |
| 5,702,669 A | 12/1997 | Green | |
| 5,741,470 A | 4/1998 | Wenzler | |
| 5,755,857 A | 5/1998 | Acharya et al. | |
| 5,779,773 A | 7/1998 | Cam et al. | |
| 5,883,199 A | 3/1999 | McCarthy et al. | |
| 5,964,927 A | 10/1999 | Graham et al. | |
| 6,156,101 A | 12/2000 | Naheiri | |
| 6,684,648 B2 | 2/2004 | Faqih | |
| 6,743,402 B2 | 6/2004 | Shimakawa | |
| 7,625,535 B2 | 12/2009 | Yamaguchi | |
| 8,110,156 B2 | 2/2012 | Ricciardi et al. | |
| 8,431,085 B2 | 4/2013 | Froderberg et al. | |
| 9,616,143 B2 | 4/2017 | Snyder et al. | |
| 10,987,443 B1 | 4/2021 | Hu et al. | |
| 2001/0033838 A1 | 10/2001 | Farmer | |
| 2002/0046569 A1 | 4/2002 | Faqih | |
| 2002/0197194 A1 | 12/2002 | Machado et al. | |
| 2004/0229340 A1 | 11/2004 | Kawai | |
| 2006/0236860 A1 | 10/2006 | Sumida et al. | |
| 2006/0249027 A1 | 11/2006 | Adolphsen et al. | |
| 2007/0209383 A1 | 9/2007 | Hutton | |
| 2008/0078289 A1 | 4/2008 | Sergi et al. | |
| 2008/0080999 A1 | 4/2008 | Bondar | |
| 2008/0289591 A1 | 11/2008 | Tessier et al. | |
| 2010/0196194 A1 | 8/2010 | Voeten et al. | |
| 2010/0291169 A1 | 11/2010 | Toreki et al. | |
| 2011/0265644 A1 | 11/2011 | Swami et al. | |
| 2012/0031268 A1 | 2/2012 | Yaghi et al. | |
| 2012/0298207 A1 | 11/2012 | Woelk et al. | |
| 2014/0119989 A1 | 5/2014 | Hayashi | |
| 2014/0251130 A1 | 9/2014 | Sprinkle et al. | |
| 2014/0290162 A1 | 10/2014 | Tanimoto | |
| 2016/0010883 A1 | 1/2016 | Jornitz et al. | |
| 2016/0130489 A1* | 5/2016 | Gilmour ................. E01C 21/00 435/252.5 |
| 2017/0056813 A1 | 3/2017 | McMahon et al. | |
| 2019/0076776 A1 | 3/2019 | Mahecha-Botero et al. | |
| 2019/0151791 A1 | 5/2019 | Awadh et al. | |
| 2019/0175971 A1 | 6/2019 | Moore et al. | |
| 2020/0148655 A1 | 5/2020 | Duff et al. | |

FOREIGN PATENT DOCUMENTS

| | | | |
|---|---|---|---|
| CN | 101224381 A | 7/2008 | |
| CN | 101549241 A | 10/2009 | |
| CN | 101773762 A | 7/2010 | |
| CN | 201632182 U | 11/2010 | |
| CN | 102173384 A | 9/2011 | |
| CN | 102219642 A | 10/2011 | |
| CN | 102302791 A | 1/2012 | |
| CN | 102921570 A | 2/2013 | |
| CN | 202802975 U | 3/2013 | |
| CN | 202933710 U | 5/2013 | |
| CN | 203183363 U | 9/2013 | |
| CN | 103386141 A | 11/2013 | |
| CN | 103394109 A | 11/2013 | |
| CN | 103394278 A | 11/2013 | |
| CN | 103657383 A | 3/2014 | |
| CN | 103667014 A | 3/2014 | |
| CN | 103706233 A | 4/2014 | |
| CN | 203507806 U | 4/2014 | |
| CN | 203564952 U | 4/2014 | |
| CN | 103800926 A | 5/2014 | |
| CN | 103801190 A | 5/2014 | |
| CN | 103908688 A | 7/2014 | |
| CN | 203749877 U | 8/2014 | |
| CN | 203750388 U | 8/2014 | |
| CN | 203750389 U | 8/2014 | |
| CN | 104014227 A | 9/2014 | |
| CN | 104275085 A | 1/2015 | |
| CN | 104307008 A | 1/2015 | |
| CN | 204261680 U | 4/2015 | |
| CN | 204447972 U | 7/2015 | |
| CN | 104815535 A | 8/2015 | |
| CN | 104946557 A | 9/2015 | |
| CN | 105132060 A | 12/2015 | |
| CN | 105327665 A | 2/2016 | |
| CN | 105664822 A | 2/2016 | |
| CN | 105462903 A * | 4/2016 | ............... C12R 1/05 |
| CN | 205300112 U | 6/2016 | |
| CN | 210721130 U | 6/2016 | |
| CN | 106139199 A | 11/2016 | |
| CN | 106421844 A | 2/2017 | |
| CN | 106475021 A | 3/2017 | |
| CN | 106582126 A | 4/2017 | |
| CN | 106754585 A * | 5/2017 | |
| CN | 107058179 A | 8/2017 | |
| CN | 206443946 U | 8/2017 | |
| CN | 206535551 U | 10/2017 | |
| CN | 107460146 A | 12/2017 | |
| CN | 206853397 U | 1/2018 | |
| CN | 107677016 A | 2/2018 | |
| CN | 207169397 U | 4/2018 | |
| CN | 207187436 U | 4/2018 | |
| CN | 107988095 A | 5/2018 | |
| CN | 207356290 U | 5/2018 | |
| CN | 207745676 U | 8/2018 | |
| CN | 207913454 U | 9/2018 | |
| CN | 108607511 A | 10/2018 | |
| CN | 208047841 U | 11/2018 | |
| CN | 208218734 U | 12/2018 | |
| CN | 109294942 A | 2/2019 | |

(56) References Cited

FOREIGN PATENT DOCUMENTS

| | | |
|---|---|---|
| CN | 109382064 A | 2/2019 |
| CN | 208448985 U | 2/2019 |
| CN | 208893903 U | 5/2019 |
| CN | 110106086 A | 8/2019 |
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U | 2/2020 |
| CN | 111117931 A | 5/2020 |
| CN | 111117932 A | 5/2020 |
| CN | 111154684 A | 5/2020 |
| CN | 111154687 A | 5/2020 |
| DE | 4236622 C1 | 3/1994 |
| EP | 0130319 A2 | 1/1985 |
| EP | 0350677 A1 | 1/1990 |
| EP | 1238718 A1 | 9/2002 |
| GB | 1472091 A | 4/1977 |
| JP | 2008114210 A | 5/2008 |
| JP | 2013172790 A | 10/2016 |
| JP | 2016221497 A | 12/2016 |
| JP | 2010259648 A | 5/2018 |
| WO | 1302478 A1 | 4/2003 |
| WO | WO 2006115199 A1 | 11/2006 |
| WO | WO2011002277 A1 | 1/2011 |
| WO | WO 2012013197 A2 | 2/2012 |
| WO | 2883598 A1 | 6/2015 |
| WO | WO-2019-136504 A1 | 7/2019 |
| WO | WO 2019236249 A1 | 12/2019 |

OTHER PUBLICATIONS

U.S. Appl. No. 17/012,769, TrackOne Bypass CON Application, filed Sep. 4, 2020, 75 pages.
U.S. Appl. No. 17/012,797, TrackOne Bypass CON Application, filed Sep. 4, 2020, 79 pages.
U.S. Appl. No. 17/012,810, TrackOne Bypass CON Application filed Sep. 4, 2020, 73 pages.
U.S. Appl. No. 17/012,828, TrackOne Bypass CON Application filed Sep. 4, 2020, 86 pages.
Yin, et al., (2016) Int. J. Hydrogen Energy, 22793-22801, "Characterization and hydrogen production performance of a novel strain Enterococcus faecium INET2 isolated from gamma irradiated sludge".
Bao, et al., (2010) Food Control, 21:695-701, "Screening of potential probiotic properties of Lactobacillus fermentum isolated from traditional dairy products".
Brown, et al., (1997) J. Ag and Food Chem. 3(45): 955-961, "Degradation of Thifensulfuron Methyl in Soil: Role of Microbial Carboxyesterase Activity".
Danko, et al., (2008) Proc. Biochem. 43:517-521, "Involvement of carbon dioxide in the aerobic biodegradation of ethylene oxide, ethene, and vinyl chloride".
Derwent-Acc-No. 2017-83105H (2017) "New Bacillus coagulans i.e. Bacillus coagulans Daoduo 4 and method (M1) for screening the B. coagulans". Abstract only, 1 pg.
Fei, et al. (2006) Annals Micro. 3(56):201-205, "Identification of Enterococcus sp. from midgut of silkworm based on biochemical and 16S rDNA sequencing analysis".
International Search Report and Written Opinion dated Oct. 28, 2020 in PCT/CN2020/101143, 10 pages.
International Search Report and Written Opinion dated Oct. 21, 2020 in PCT/CN2020/101141, 12 pages.
International Search Report and Written Opinion dated Oct. 27, 2020 in PCT/CN2020/101138, 11 pages.
International Search Report and Written Opinion dated Oct. 28, 2020 in PCT/CN2020/101144, 10 pages.
International Search Report and Written Opinion dated Oct. 28, 2020 in PCT/CN2020/101139, 11 pages.
International Search Report and Written Opinion dated Dec. 16, 2020 in PCT/CN2020/101142, 11 pages.
International Search Report and Written Opinion, in PCT/CN2020/101140 dated Dec. 21, 2020, 11 pages.
International Search Report and Written Opinion, in PCT/CN2020/100143 dated Dec. 21, 2020, 9 pages.
International Search Report and Written Opinion, in PCT/CN2020/100125 dated Dec. 23, 2020, 9 pages.
International Search Report and Written Opinion, in. PCT/CN2020/100115 dated Dec. 16, 2020, 11 pages.
International Search Report and Written Opinion, in. PCT/CN2020/100119 dated Dec. 17, 2020, 9 pages.
International Search Report and Written Opinion, in PCT/CN2020/100144 dated Dec. 18, 2020, 10 pages.
Kahm et al., 2018 "Lyapunov exponents with Model Predictive Control for exothermic batch reactors" IFAC-PapersOnline, 51, 417-422.
Khatiwala, et al. (2008) J. Polym. Environ. 16:61-67, "Biodegradation of poly(ε-caprolactone)(PCL) film by Alcaligenes faecalis".
Liao, et al., (2001) Environ. Tech. 22:165-173, "Decomposition of ethylene oxide in the RF plasma environment".
Perez-Cano, et al., (2010) Immunobiology 215:996-1004, "In vitro immunomodulatory activity of Lactobacillus fermentum CECT5716 and Lactobacillus salivarius CECT5713: two probiotic strains isolated from human breast milk".
Poelarends, et al., (1999) J. Bact. 7(181):2050-2058, "Degradation of 1, 2-Dibromoethane by Mycobacterium sp. Strain GP1".
Shin, et al., (2016) Anaerobe 39:14-18, "Clostridium kogasensis sp. nov., a novel member of the genus Clostridium, isoloated from soil under a corroded gas pipeline".
Sutton, et al. (2018) F1000 Research 7:1-26, "Enterobacter hormaechei subsp. hoffmannii subsp. nov., Enterobacter hormaechei subsp. xiangfangensis comb. nov., Enterobacter roggenkampii sp. nov., and Enterobacter muelleri is a later heterotypic synonym of Enterobacter asburiae based on computational analysis of sequenced Enterobacter genomes".
Taylor, et al., (2010) Appl. Micro. Biotech. 87:2293-2302, "Extendin the alkene substrate range of vinyl chloride utilizing Nocardioides sp. strain JS614 with ethene oxide".
U.S. Appl. No. 17/012,857, TrackOne Bypass CON Application filed Sep. 4, 2020, 148 pages.
U.S. Appl. No. 17/002,500, TrackOne Bypass CON Application filed Aug. 25, 2020, 61 pages.
U.S. Appl. No. 17/002,523, TrackOne Bypass CON Applicationc filed Aug. 25, 2020, 72 pages.
U.S. Appl. No. 17/002,529, TrackOne Bypass CON Application filed Aug. 25, 2020, 64 pages.
U.S. Appl. No. 17/002,540, TrackOne Bypass CON Application filed Aug. 25, 2020, 89 pages.
U.S. Appl. No. 17/004,730, TrackOne Bypass CON Application filed Aug. 27, 2020, 77 pages.
U.S. Appl. No. 17/012,864, TrackOne Bypass CON Application filed Sep. 4, 2020, 78 pages.
U.S. Appl. No. 17/004,903, TrackOne Bypass CON Application filed Aug. 27, 2020, 67 pages.
U.S. Appl. No. 17/004,930, TrackOne Bypass CON Application filed Aug. 27, 2020, 80 pages.
U.S. Appl. No. 17/004,971, TrackOne Bypass CON Application filed Aug. 27, 2020, 75 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
agagtttgat cctggctcag                                            20

<210> SEQ ID NO 2
<211> LENGTH: 19
<212> TYPE: DNA
<213> ORGANISM: Artificial Sequence
<220> FEATURE:
<223> OTHER INFORMATION: Synthetic construct

<400> SEQUENCE: 2
ggttaccttg ttacgactt                                             19

<210> SEQ ID NO 3
<211> LENGTH: 1432
<212> TYPE: DNA
<213> ORGANISM: Alcaligenes faecalis

<400> SEQUENCE: 3
gctttaacac atgcaagtcg aacggcagca cgcagagagc ttgctctctt ggtggcgagt   60
```

```
ggcggacggg tgagtaatat atcggaacgt gcccagtagc gggggataac tactcgaaag    120
agtggctaat accgcatacg ccctacgggg aaaggggggg gatcgcaaga cctctcacta    180
ttggagcggc cgatatcgga ttagctagtt ggtggggtaa aggctcacca aggcaacgat    240
ccgtagctgg tttgagagga cgaccagcca cactgggact gagacacggc ccagactcct    300
acgggaggca gcagtgggga attttggaca atggggaaa ccctgatcca gccatcccgc     360
gtgtatgatg aaggccttcg ggttgtaaag tacttttggc agagaagaaa aggcatcccc    420
taatacggga tgctgctgac ggtatctgca gaataagcac cggctaacta cgtgccagca    480
gccgcggtaa tacgtagggt gcaagcgtta atcggaatta ctgggcgtaa agcgtgtgta    540
ggcggttcgg aaagaaagat gtgaaatccc agggctcaac cttggaactg cattttttaac   600 tgccgagcta gagtatgtca gaggggggta gaattccacg tgtagcagtg aaatgcgtag    660
atatgtggag gaataccgat ggcgaaggca gcccctggg ataatactga cgctcagaca     720
cgaaagcgtg gggagcaaac aggattagat accctggtag tccacgccct aaacgatgtc    780
aactagctgt tggggccgtt aggccttagt agcgcagcta acgcgtgaag ttgaccgcct    840
ggggagtacg gtcgcaagat taaaactcaa aggaattgac ggggacccgc acaagcggtg    900
gatgatgtgg attaattcga tgcaacgcga aaaaccttac ctaccttga catgtctgga    960 aagccgaaga gatttggcag tgctcgcaag agaaccggaa cacaggtgct gcatggctgt   1020
cgtcagctcg tgtcgtgaga tgttgggtta agtcccgcaa cgagcgcaac ccttgtcatt   1080
agttgctacg caagagcact ctaatgagac tgccggtgac aaaccggagg aaggtgggga   1140
tgacgtcaag tcctcatggc ccttatgggt agggcttcac acgtcataca atggtcggga   1200
cagagggtcg ccaacccgcg aggggggagcc aatctcagaa accgatcgt agtccggatc    1260 gcagtctgca actcgactgc gtgaagtcgg aatcgctagt aatcgcggat cagaatgtcg   1320
cggtgaatac gttcccgggt cttgtacaca ccgcccgtca ccatggga gtgggtttca     1380 ccagaagtag gtagcctaac cgcaaggagg gcgctaccac ggtgatgatg tc          1432
```

<210> SEQ ID NO 4
<211> LENGTH: 1432
<212> TYPE: DNA
<213> ORGANISM: Alcaligenes faecalis EO-05

<400> SEQUENCE: 4

```
gctttaacac atgcaagtcg aacggcagca cgcagagagc ttgctctctt ggtggcgagt     60
ggcggacggg tgagtaatat atcggaacgt gcccagtagc gggggataac tactcgaaag    120
agtggctaat accgcatacg ccctacgggg aaaggggggg gatcgcaaga cctctcacta    180
ttggagcggc cgatatcgga ttagctagtt ggtggggtaa aggctcacca aggcaacgat    240
ccgtagctgg tttgagagga cgaccagcca cactgggact gagacacggc ccagactcct    300
acgggaggca gcagtgggga attttggaca atggggaaa ccctgatcca gccatcccgc     360
gtgtatgatg aaggccttcg ggttgtaaag tacttttggc agagaagaaa aggcatcccc    420
taatacggga tgctgctgac ggtatctgca gaataagcac cggctaacta cgtgccagca    480
gccgcggtaa tacgtagggt gcaagcgtta atcggaatta ctgggcgtaa agcgtgtgta    540
ggcggttcgg aaagaaagat gtgaaatccc agggctcaac cttggaactg cattttttaac   600 tgccgagcta gagtatgtca gaggggggta gaattccacg tgtagcagtg aaatgcgtag    660
atatgtggag gaataccgat ggcgaaggca gcccctggg ataatactga cgctcagaca     720
cgaaagcgtg gggagcaaac aggattagat accctggtag tccacgccct aaacgatgtc    780
```

```
aactagctgt tggggccgtt aggccttagt agcgcagcta acgcgtgaag ttgaccgcct      840
ggggagtacg gtcgcaagat taaaactcaa aggaattgac ggggacccgc acaagcggtg      900
gatgatgtgg attaattcga tgcaacgcga aaaaccttac ctacccttga catgtctgga     960
aagccgaaga gatttggcag tgctcgcaag agaaccggaa cacaggtgct gcatggctgt    1020
cgtcagctcg tgtcgtgaga tgttgggtta agtcccgcaa cgagcgcaac ccttgtcatt    1080
agttgctacg caagagcact ctaatgagac tgccggtgac aaaccggagg aaggtgggga    1140
tgacgtcaag tcctcatggc ccttatgggt agggcttcac acgtcataca atggtcggga    1200
cagagggtcg ccaacccgcg aggggagcc aatctcagaa acccgatcgt agtccggatc    1260
gcagtctgca actcgactgc gtgaagtcgg aatcgctagt aatcgcggat cagaatgtcg   1320
cggtgaatac gttcccgggt cttgtacaca ccgcccgtca caccatggga gtgggtttca    1380
ccagaagtag gtagcctaac cgcaaggagg gcgctaccac ggtgatgatg tc            1432
```

ALCALIGENES FAECALIS FOR DEGRADING ETHYLENE OXIDE

CROSS-REFERENCE TO RELATED PATENT APPLICATIONS

This application is a Bypass Continuation of PCT/CN2020/101139, filed Jul. 9, 2020, which application claims the benefit of Chinese Patent Application No. 202010064718.2, filed on Jan. 20, 2020 and Chinese Patent Application No. 202010064633.4, filed on Jan. 20, 2020, the entire contents of which are incorporated herein by reference in their entirety for all purposes.

TECHNICAL FIELD

The present disclosure relates to the field of microbial technology, and more particularly to a strain of *Alcaligenes faecalis* capable of degrading ethylene oxide and uses thereof.

SEQUENCE STATEMENT

Incorporated by reference herein in its entirety is the Sequence Listing entitled "1211_CK05_ST25_PCT" created Jun. 9, 2020, size of 4.54 kilobytes.

BACKGROUND

Ethylene oxide (EO) is among the most important petrochemical products in the modern industries and plays a significant role in the medical sterilization industry thanks to its strong penetrability and ability to perform coupling reactions with biological macromolecules. In addition, ethylene oxide sterilization has a low cost and can be used for industrial-grade sterilization in a large scale, making it by far one of the most important low-temperature sterilizers. However, ethylene oxide is extremely active, flammable, explosive, and globally recognized as a carcinogen. Large quantities of ethylene oxide are found in wastewater from petrochemical industries and need to be decontaminated.

At present, oxidization of ethylene oxide with sulfuric acid is the primary way of ethylene oxide decontamination process in countries such as China. However, it fails to meet the requirements of full decontamination as, disadvantageously, a large amount of industrial wastewater containing ethylene oxide will be discharged after the chemical treatment.

There is an urgent and long-felt need to find a way of ethylene oxide decontamination. Microbial degradation of harmful substances plays an important role in the chemical industry. However, there are few studies on the use of microorganisms to degrade ethylene oxide and no reports of bacteria or their uses on effective degradation of ethylene oxide.

SUMMARY

In view of this, the present disclosure provides an *Alcaligenes faecalis* strain that can effectively degrade ethylene oxide, which can be used to degrade ethylene oxide pollutants, e.g., in sewage, sludge, exhaust gas, or wastewater, especially industrial (such as industries related to petroleum and derivative products), medical treatment (such as ethylene oxide sterilant) and other sewage or wastewater. Therefore, it may greatly improve the decontamination processes of ethylene oxide and reduce environmental risks, such as public health risk.

In one of the aspects of the present disclosure, an *Alcaligenes faecalis* strain EO-05 with the Deposit Number of CGMCC No. 18435 is provided. The *Alcaligenes faecalis* EO-05 can effectively degrade ethylene oxide.

In one of the aspects of the present disclosure, an *Alcaligenes faecalis* strain comprising the 16S rDNA sequence of SEQ ID NO: 4 is provided. The *Alcaligenes faecalis* strain can effectively degrade ethylene oxide.

In one of the aspects of the present disclosure, it provides a degradation agent for degrading ethylene oxide, comprising the *Alcaligenes faecalis* strain EO-05 or the *Alcaligenes faecalis* strain comprising the 16S rDNA sequence of SEQ ID NO: 4.

In some of the embodiments, the degradation agent is prepared by culturing the *Alcaligenes faecalis* strain EO-05 or the *Alcaligenes faecalis* strain comprising the 16S rDNA sequence of SEQ ID NO: 4.

In some of the embodiments, a final concentration of the *Alcaligenes faecalis* strain EO-05 or the *Alcaligenes faecalis* strain comprising the 16S rDNA sequence of SEQ ID NO: 4 in the degradation agent is at least $10^8$ cfu/mL, or from $10^8$ cfu/mL to $10^{10}$ cfu/mL.

In one of the aspects of the present disclosure, it provides a method for preparing a degradation agent for degrading ethylene oxide, comprising: inoculating the *Alcaligenes faecalis* strain EO-05 or the *Alcaligenes faecalis* strain comprising the 16S rDNA sequence of SEQ ID NO: 4 and incubating the inoculated medium thereby obtaining the degradation agent. In some aspects, the strain is inoculated into tryptone soybean broth culture medium. In some aspects, the strain is incubated for 48 hours of incubation at 37° C. and 200 rpm.

In one of the aspects of the present disclosure, it provides a method for biodegrading ethylene oxide, comprising using the *Alcaligenes faecalis* strain EO-05, the *Alcaligenes faecalis* strain comprising the 16S rDNA sequence of SEQ ID NO: 4, or the aforementioned degradation agent to degrade ethylene oxide.

In one of the aspects of the present disclosure, it provides a method for decreasing the amount of ethylene oxide in material, comprising adding to a material comprising ethylene oxide an amount a pure culture of an *Alcaligenes faecalis* strain bacterium, allowing the bacterium to degrade the ethylene oxide, thereby decreasing the amount of ethylene oxide, wherein the 16S rDNA sequence of the *Alcaligenes faecalis* strain bacterium is SEQ ID NO: 4.

In a further aspect of the method, the *Alcaligenes faecalis* strain bacterium is capable of using ethylene oxide as a carbon source and is capable of growing normally with ethylene oxide as the sole carbon source in the culture.

In a further aspect of the method, the *Alcaligenes faecalis* strain bacterium is *Alcaligenes faecalis* strain EO-05 with the Deposit Number of CGMCC No. 18435.

The degradation rate in the methods is at least 10%, 15%, 20%, 25%, 30%, 35%, 40%, 50%, 60%, 70%, 75%, 80%, 90%, 95%, 100%, 125%, 150%, 200%, or 500% greater relative to the degradation rate of ethylene oxide in the absence of the *Alcaligenes faecalis* strain EO-05 or *Alcaligenes faecalis* strain comprising the 16S rDNA sequence of SEQ ID NO: 4.

In some of the embodiments, the method is used for degrading ethylene oxide in sewage, sludge, exhaust gas, or wastewater, and comprises: applying the *Alcaligenes faecalis* strain EO-05, the *Alcaligenes faecalis* strain comprising the 16S rDNA sequence of SEQ ID NO: 4 or the degradation agent aforementioned to the sewage or wastewater. The sewage or wastewater may be industrial (such as industries related to petroleum and derivative products), medical (such as ethylene oxide sterilant) or other sewage or wastewater.

In some embodiments, the method comprises incubating the strain in liquid TSB medium to a concentration from $10^{10}$ cfu/mL to $10^{12}$ cfu/mL, to obtain an activation liquid for degrading ethylene oxide.

In one embodiment, the method comprises a concentration of the strain for degrading ethylene oxide ranging from $10^8$ cfu/mL to $10^{10}$ cfu/mL.

In some of the embodiments, the using an *Alcaligenes faecalis* of the invention to degrade ethylene oxide in the method comprises: inoculating the *Alcaligenes faecalis* strain EO-05 or the *Alcaligenes faecalis* strain comprising the 16S rDNA sequence of SEQ ID NO: 4 into tryptone soy broth culture medium for 48 hours of incubation at 37° C. and 200 rpm to obtain an *Alcaligenes faecalis* EO-05 culture; and using the *Alcaligenes faecalis* EO-05 culture to degrade ethylene oxide.

In one of the aspects of the present disclosure, it provides use of the *Alcaligenes faecalis* strain EO-05 the *Alcaligenes faecalis* strain comprising the 16S rDNA sequence of SEQ ID NO: 4, the degradation agents, or a degradation agent prepared according to the method aforementioned in degradation of ethylene oxide.

In one of the aspects of the present disclosure, it provides use of the *Alcaligenes faecalis* strain EO-05 or the *Alcaligenes faecalis* strain comprising the 16S rDNA sequence of SEQ ID NO: 4 in the preparation of a degradation agent for degrading ethylene oxide.

The present disclosure provides an *Alcaligenes faecalis* strain EO-05 or the *Alcaligenes faecalis* strain comprising the 16S rDNA sequence of SEQ ID NO: 4 that can degrade ethylene oxide, which can be used to treat pollution, for example, to treat industrial or medical sewage or wastewater containing ethylene oxide. The strain EO-05 or other strains of the invention can be cultivated in a very simple way and efficiently degrade high-concentration ethylene oxide in a short period of time without other carbon sources. Therefore, the present disclosure may greatly improve the decontamination processes of ethylene oxide.

In a further aspect of the present disclosure, there is also provided a method for purifying ethylene oxide-degrading potential bacteria, comprising:

incubating a suspension containing at least one original strain *Alcaligenes faecalis* strain bacterium into a first enrichment medium to obtain a bacterial suspension, wherein the first enrichment medium is liquid TSB medium containing ethylene oxide;

inoculating and incubating the bacterial suspension into a screening and purification medium to obtain an ethylene oxide-degrading predominant strain, wherein the screening and purification medium is TSB agar medium containing ethylene oxide; and inoculating and incubating the ethylene oxide-degrading predominant strain into a second enrichment medium to obtain an ethylene oxide-degrading potential bacteria, wherein the second enrichment medium is liquid TSB medium containing no ethylene oxide.

In one embodiment, the method comprises mixing sewage or sludge containing the original strain with phosphate buffer, and filtering for removal of precipitate to obtain the suspension.

In one embodiment, the first enrichment medium is prepared as follows: sterilizing liquid TSB medium, cooling the medium to room temperature, and adding liquid ethylene oxide to the medium. The liquid TSB medium contains 17 g/L tryptone, 3 g/L soy peptone, 2.5 g/L of dipotassium hydrogen phosphate and 2.5 g/L of glucose, and has pH 7.4.

In one embodiment, the screening and purification medium is prepared as follows: sterilizing TSB agar medium, cooling the medium to 50° C. to 56° C., and adding liquid ethylene oxide to the medium. The TSB agar medium contains 2.5 g of dipotassium hydrogen phosphate, 2.5 g of glucose and 15 g/L agar, and has pH 7.4.

In one embodiment, the second enrichment medium is prepared as follows: sterilizing TSB medium, and cooling the medium to room temperature. The second enrichment medium does not contain ethylene oxide.

In one embodiment, the suspension is incubated in the first enriched enrichment medium having a low concentration of ethylene oxide for 24 to 48 hours, and the bacterial suspension is incubated on the screening and purification medium plate having a low concentration of ethylene oxide for at least 24 hours. The low concentration of ethylene oxide in the first enriched enrichment medium and the screening and purification medium plate may be range from 10 mg/L to 500 mg/L, e.g., 100 mg/L.

In further aspect of the present disclosure, there is also provided a method for producing a strain for degrading ethylene oxide, comprising:

inoculating at least one original strain of *Alcaligenes faecalis* into ethylene oxide-tolerance acclimation mediums for subculture, to obtain an ethylene oxide-degrading predominant strain, wherein the ethylene oxide-tolerance acclimation mediums are Sabouraud's agar mediums containing ethylene oxide with a serially increasing concentration during subculture; and inoculating the ethylene oxide-degrading predominant strain into ethylene oxide-degradation acclimation mediums for subculture, wherein the ethylene oxide-degradation acclimation mediums are Sabouraud's agar mediums containing ethylene oxide and a carbon source with a serially decreasing concentration in the ethylene oxide-degradation acclimation mediums during subculture.

In one embodiment, the concentration of carbon source serially decreases from 20 g/L to 0 mg/L during subculture.

In one embodiment, the concentration of the carbon source in the ethylene oxide-degradation acclimation mediums serially decreases from 50%, to 0% during subculture.

In one embodiment, the original strain is incubated at a temperature of 37° C. in the ethylene oxide-tolerance acclimation medium.

In one embodiment, the ethylene oxide-degrading predominant strain is incubated at a temperature of 37° C. in ethylene oxide-degradation acclimation mediums.

In one embodiment, the original strain is subcultured in ethylene oxide-tolerance acclimation mediums containing 0 mg/L to 100 mg/L, 100 mg/L to 200 mg/L, 200 mg/L to 500 mg/L, 500 mg/L to 800 mg/L ethylene oxide for 24 to 48 hours serially and respectively.

In one embodiment, the original strain is subcultured in the ethylene oxide-tolerance acclimation mediums containing 100 mg/L, 200 mg/L, 500 mg/L, 800 mg/L ethylene oxide serially and respectively.

In one embodiment, the ethylene oxide-degrading predominant strain is incubated in the second enrichment medium for at least 24 hours to obtain ethylene oxide-degrading potential bacteria.

In one embodiment, the ethylene oxide-degrading predominant strain is obtained by:

inoculating the original strain into the first ethylene oxide-tolerance acclimation medium plate containing 100 mg/L ethylene oxide for subculture, and incubating the first plate in an incubator at 37° C. for 24 to 48 hours; picking a first single colony with a largest radius on the first plate and inoculating the first single colony into the second ethylene oxide-tolerance acclimation medium plate with 100 to 200 mg/L ethylene oxide for subculture, and incubating the second plate in an incubator at 37° C. for 24 to 48 hours; picking a second single colony with a largest radius on the second plate and inoculating the second single colony into the third ethylene oxide-tolerance acclimation medium plate with 200 to 500 mg/L ethylene oxide for subculture, and incubating the third plate in an incubator at 37° C. for 24 to 48 hours; picking a third single colony with a largest radius on the third plate and inoculating the third single colony into the fourth ethylene oxide-tolerance acclimation medium plate with 500 to 800 mg/L ethylene oxide for subculture, and incubating the fourth plate in an incubator at 37° C. for 24 to 48 hours; finally picking a fourth single colony with a largest radius on the fourth ethylene oxide-tolerance acclimation medium plate containing 500 to 800 mg/L ethylene oxide to obtain the ethylene oxide-degrading predominant strain.

In one embodiment, the ethylene oxide-tolerance acclimation mediums are prepared as follows: adding liquid ethylene oxide into a sterilized Sabouraud's agar medium to a final concentration from 100 mg/L to 800 mg/L, wherein the ethylene oxide-tolerance acclimation mediums contain 10 g/L peptone, 40 g/L of glucose, and 15 g/L agar, and pH of 5.4 to 5.8.

In one embodiment, the sterilized Sabouraud's agar mediums are heated to melt, cooled to 50° C. to 56° C., and mixed with liquid ethylene oxide.

In one embodiment, the ethylene oxide-degrading predominant strain is serially and respectively subcultured in the ethylene oxide-degradation acclimation mediums containing 20 g/L, 12 g/L, 4 g/L, and 0 g/L the carbon source for 24 to 48 hours.

In one embodiment, the ethylene oxide-degradation acclimation mediums have glucose as the carbon source.

In one embodiment, the ethylene oxide-degrading predominant strain is inoculated into the ethylene oxide-degradation acclimation medium plates having 500 mg/L to 800 mg/L ethylene oxide and a carbon source with a serially decreasing concentration, and subcultured in an incubator at a temperature from 25° C. to 37° C. for 24 to 48 hours respectively and serially; and picking a single colony with a largest radius to obtain the strain for degrading ethylene oxide.

In one embodiment, the strain for degrading ethylene oxide is obtained as follows: inoculating the ethylene oxide-degrading predominant strain into the first ethylene oxide-degradation acclimation medium plate containing 800 mg/L ethylene oxide and 20 g/L carbon source, and incubating the first plate in an incubator at 37° C. for 24 to 48 hours; picking a first single colony with a largest radius on the first plate, inoculating the first single colony into the second ethylene oxide-degradation acclimation medium plate containing 800 mg/L ethylene oxide and 12 g/L carbon source, and incubating the second plate in an incubator at 37° C. for 24 to 48 hours; picking a second single colony with a largest radius on the second plate, inoculating the second single colony into the third ethylene oxide-degradation acclimation medium plate containing 800 mg/L ethylene oxide and 4 g/L carbon source, and incubating the third plate in an incubator at 37° C. for 24 to 48 hours; picking a third single colony with a largest radius on the third plate, inoculating the third single colony into the fourth ethylene oxide-degradation acclimation medium plate containing 800 mg/L ethylene oxide and 0 g/L carbon source, and incubating the fourth plate in an incubator at 37° C. for 24 to 48 hours; finally picking a fourth single colony with a largest radius on the fourth ethylene oxide-degradation acclimation medium plate containing 800 mg/L ethylene oxide and 0 g/L carbon source to obtain the strain for degrading ethylene oxide.

The *Alcaligenes faecalis* EO-05 strain was deposited on Aug. 29, 2019 at China General Microbiological Culture Collection Center, with the deposit number being CGMCC No. 18435 and the deposit address being Institute of Microbiology of Chinese Academy of Sciences, NO. 1 West Beichen Road, Beijing 100101, China.

DETAILED DESCRIPTION OF EMBODIMENTS

Detailed description will be given below with referral to the accompanying figures to facilitate understanding of the present application. Preferred embodiments are shown in the figures. However, the present application may be implemented in various ways, without being limited to the examples presented in the description. The purpose of these embodiments is merely for illustration and better comprehension of the present disclosure.

Unless otherwise defined, all the technical and scientific terms herein shall be understood as the same meaning with those commonly accepted by a person skilled in the art. Such terms, as used herein, are for the purpose of describing specific embodiments of, without limiting, the present application. The term "and/or" as used herein refers to any and all combinations of one or more items recited.

Example 1

Screening and Purification of Bacteria Strains with EO-Degrading Ability

This is an example of the screening and purification of bacteria strains with EO-degrading ability.

A sample of the sludge mixture was collected at the sewage outlet of a suburban sewage treatment plant in Guangzhou, Guangdong Province, and used for the screening and purification experiments of this example.

10.0 g of the sludge mixture sample was weighed, added with 100 mL of 0.03 mol/L phosphate buffer, well mixed, allowed to stand for 120 min for clarification, and filtered to remove large particles of sediment and obtain a suspension.

Liquid enrichment medium (also known as TSB medium) was prepared as follows: 17 g of tryptone, 3 g of soy peptone, 5 g of sodium chloride, 2.5 g of dipotassium hydrogen phosphate and 2.5 g of glucose were mixed, adjusted to a pH of 7.4, and added to 1000 mL of distilled water, thoroughly mixed. Portions of 250 ml of the prepared medium was added to 500 mL Erlenmeyer flasks, sterilized at 121° C. for 20 min, and cooled to room temperature. Pure ethylene oxide liquid was placed on an ice box and 28 µL of ethylene oxide liquid was taken and injected into the sterilized medium by a sealed syringe, providing 100 mg/L of ethylene oxide in the medium complying with the national emission standard.

1 mL of the suspension was added to each of 4 test tubes containing 10 mL of liquid enrichment medium and placed in a shaker for oxygen-consuming enrichment culture for 24-48 h (200 rpm, 37° C.).

Selection medium and selection culture plates were prepared as follows: 17 g of tryptone, 3 g of soy peptone, 5 g of sodium chloride, 2.5 g of dipotassium hydrogen phosphate, 2.5 g of glucose and 15 g of agar were mixed, adjusted to a pH of 7.4, and added to 1000 mL of distilled water, thoroughly mixed. Portions of 250 ml of the prepared selection medium was added into 500 mL Erlenmeyer flasks, sterilized at 121° C. for 20 minutes, and cooled to about 50-56° C. 28 µL of ethylene oxide liquid was injected into the sterilized medium by a sealed syringe to make a selection culture plate.

Figure 1:
FIG. 1 shows a photo of bacterial colony growth of the EO-degrading potential bacteria in enrichment medium without ethylene oxide at a constant temperature of 37° C. for 48 hours, wherein the EO-degrading potential bacteria was obtained by the screening and purification processes according to Example 1.

The dominant strains in the liquid enrichment medium were streaked on the selection culture plate for separation of the EO-degrading potential bacteria. As shown in FIG. 1, at 48 hours of culture, the colony was characterized by gray-white color, uneven edges, spreading growth, and with a colony diameter of 4.0-6.0 mm and blue-green fluorescent pigments.

Single colonies were selected and cultured in the liquid enrichment medium without ethylene oxide for 24 hours to obtain EO-degrading potential bacteria, which were preserved at −80° C. using the glycerin preservation method (culture medium: 50% glycerol=1:

Example 2

Characterization and Identification of EO-Degrading Bacteria Strains

This is an example of characterization and identification of EO-degrading bacteria strains, using the following identification methods:

Morphological characterization: including observation of colony morphology, microscopic morphology, culture characteristics and Gram staining;

Physiological and biochemical characterization: including nutrition type, nitrogen and carbon source utilization capacity, and biochemical tests;

Molecular biological characterization (The DNA in the genome that produces the ribosomal RNA is called the "rRNA gene" or simply "rDNA." 16s rDNA sequencing): including the procedure of bacterial culture, bacterial DNA extraction, PCR amplification, 16s rDNA sequencing and sequence alignment analysis, wherein the primer pair for PCR amplification was as follows:

```
Upstream primer 27F:
5'-AGAGTTTGATCCTGGCTCAG-3', as shown in

SEQ ID NO: 1;
and

Downstream primer 1492R:
5'-GGTTACCTTGTTACGACTT-3', as shown in

SEQ ID NO: 2.
```

The above characterization and identification methods are well known to those skilled in the art.

Figure 2:
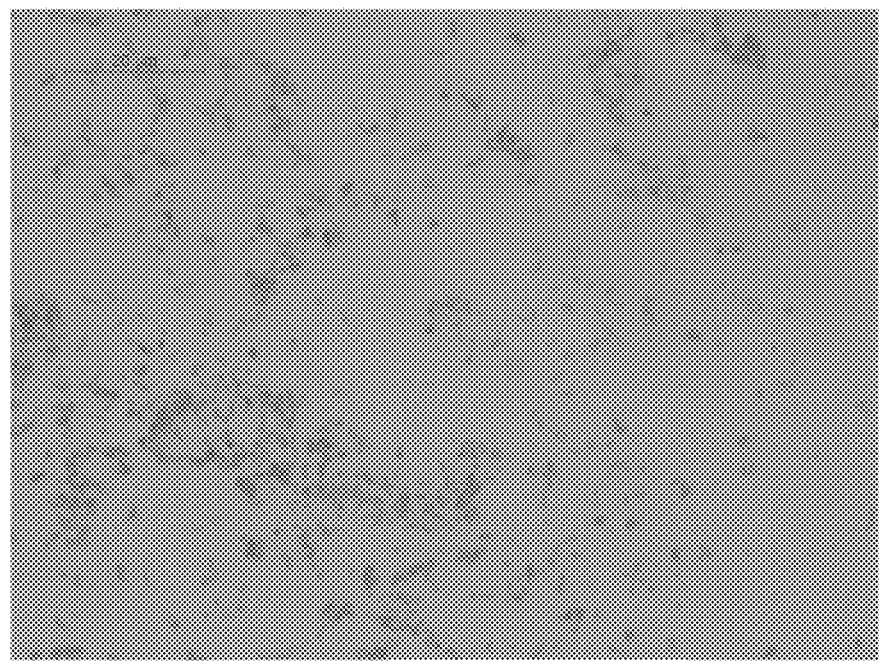
FIG. 2 shows the Gram staining result of the EO-degrading potential bacteria in the identification tests according to Example 2, wherein the EO-degrading potential bacteria was obtained by the screening and purification processes according to Example 1.
Figure 3:
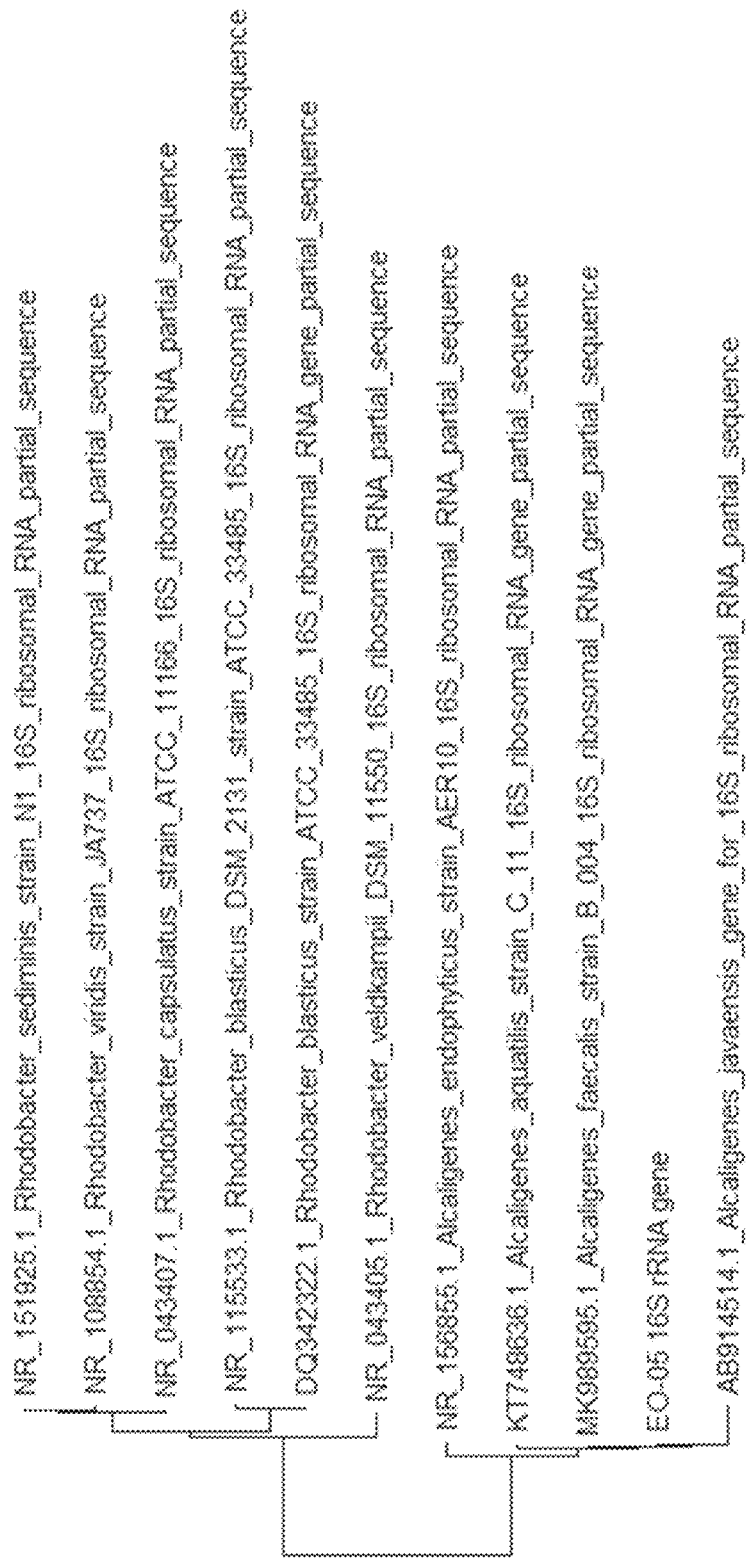
FIG. 3 shows the phylogenetic evolution diagram of the EO-degrading potential bacteria in the identification tests according to Example 2, wherein the EO-degrading potential bacteria was obtained by the screening and purification processes according to Example 1.

The characterization and identification results are as follows:

Morphological characteristics: gray-white colonies, uneven edges, spreading growth, colony diameter 4.0-6.0 mm, with blue-green fluorescent pigment. Under microscope, the bacterial cells were short rods or spherical-shaped, separately arranged and without spores. The Gram stain gave a negative result as shown in FIG. 2;

Molecular biological characteristics: the sequencing result of 16s rDNA is shown in SEQ ID NO: 3; the 16S rDNA sequence was subjected to nucleotide sequence alignment analysis by BLAST and showed a 99% sequence homology with *Alcaligenes faecalis*. The phylogenetic tree of this strain is shown in FIG. 3.

According to the characterization results of morphology, physiology, biochemistry, and molecular biology, EO-degrading potential bacteria strain obtained by screening and purification according to Example 1 was *Alcaligenes faecalis*.

Example 3

Inductive Acclimation of EO-Degrading Potential Bacteria Strains

This is an example of inductive acclimation of EO-degrading potential bacteria strains, including inductive acclimation of ethylene oxide tolerance and acclimation of ethylene oxide degradation ability.

Phase I: Inductive Acclimation of Ethylene Oxide Tolerance

The tolerance acclimation medium and culture plates were prepared as follows: 10 g of peptone, 40 g of glucose and 15 g of agar were mixed, adjusted to a pH of 5.4-5.8, and added to 1000 mL of distilled water, thoroughly mixed. The prepared culture medium was divided into portions of 250 mL and sterilized at 121° C. for 20 min. Before use, the medium was heated to melt, allowed to cool to about 50-56° C., and added with 25 mg, 50 mg, 125 mg or 200 mg of ethylene oxide respectively by a sealed syringe to make medium plates with four different concentrations of ethylene oxide (100 mg/L, 200 mg/L, 500 mg/L or 800 mg/L).

Using the method of plate streaking, the EO-degrading potential bacteria obtained from Example 1 was inoculated onto the tolerance acclimation medium with 100 mg/L ethylene oxide and incubated at a constant temperature of 37° C. for 48 h. Then the single colony with the largest radius was selected and subcultured onto the tolerance acclimation medium with 200 mg/L ethylene oxide and incubated at 37° C. for 48 h. Again, the single colony with the largest colony radius on the plate was selected and subcultured onto the tolerance acclimation medium with 500 mg/L ethylene oxide and incubated at a constant temperature of 37° C. for 48 h. The single colony with the largest colony radius on the plate was selected and subcultured onto the tolerance acclimation medium with 800 mg/L ethylene oxide and incubated at a constant temperature of 37° C. for 48 h. Then the single colony with the largest colony radius on the plate was selected as a strain with tolerance against high concentration of ethylene oxide.

Phase II: Inductive Acclimation of Ethylene Oxide Degradation Ability

The degradation acclimation medium and culture plates were prepared as follows: 10 g of peptone, glucose (20 g, 12 g, 4 g, or 0 g) and 15 g of agar were mixed, adjusted to a pH of 5.4-5.8, and added to 1000 mL of distilled water, thoroughly mixed to make mediums of four different carbon contents (50%, 30%, 10%, or 0%). The medium prepared as above were divided into 250 ml portions and sterilized at 121° C. for 20 min. Before use, the medium was heated to melt, allowed to cool to about 50-56° C., and added with 200 mg of ethylene oxide by a sealed syringe to make four types of culture plates with different amounts of carbon source (50%, 30%, 10%, or 0%) and 800 mg/L of ethylene oxide.

Using the method of plate streaking, the strain with tolerance against high concentration of ethylene oxide obtained from Phase I was inoculated onto the degradation acclimation medium with 800 mg/L ethylene oxide and 50% carbon source, and incubated at a constant temperature of 37° C. for 48 h. Then the single colony with the largest radius was selected and subcultured onto the degradation acclimation medium with 800 mg/L ethylene oxide and 30% carbon source and incubated at 37° C. for 48 h. Again, the single colony with the largest colony radius on the plate was selected and subcultured onto the degradation acclimation medium with 800 mg/L ethylene oxide and 10% carbon source and incubated at a constant temperature of 37° C. for 48 h. The single colony with the largest colony radius on the plate was selected and subcultured onto the degradation acclimation medium with 800 mg/L ethylene oxide and 0% carbon source and incubated at a constant temperature of 37° C. for 48 h. The single colony with the largest colony radius on the plate was selected as a strain with strong tolerance and degradation ability against high concentration of ethylene oxide, which was then designated as the EO-05 strain.

The EO-05 strain was preserved on agar medium slope with corresponding nutrients at −80° C. using the glycerin preservation method (culture medium: 50% glycerol=1:1).

The results of Phase I and Phase II inductive acclimation of the bacteria strains were summarized in Table 1. It shows that the strain EO-05 was obtained with strong tolerance and degradation ability against high concentration of ethylene oxide by gradual control of the cultivation conditions of the dominant strains against ethylene oxide. The EO-05 strain was able to use ethylene oxide as a carbon source and grow normally with ethylene oxide being the sole carbon source in the culture.

TABLE 1

Experiment results of induced acclimation of EO tolerance (Phase I) and EO degradation ability (Phase II)

| | Phase I | | | | Phase II | | | |
|---|---|---|---|---|---|---|---|---|
| Carbon source (%) | 100 | 100 | 100 | 100 | 50 | 30 | 10 | 0 |
| EO concentration (mg/L) | 100 | 200 | 500 | 800 | 800 | 800 | 800 | 800 |
| Colony growth | + | + | + | + | + | + | + | + |

Note:
"+" represents bacterial growth.

The 16s rDNA sequence of the strain EO-05 acclimated in Example 3 was sequenced and the sequencing result is shown in SEQ ID NO: 4.

The *Alcaligenes faecalis* EO-05 strain was deposited on Aug. 29, 2019 at China General Microbiological Culture Collection Center, with the deposit number being CGMCC No. 18435 and the deposit address being Institute of Microbiology of Chinese Academy of Sciences, NO. 1 West Beichen Road, Beijing 100101, China.

Example 4

Comparative Test

This is an example testing the ability of the EO-05 strain to degrade ethylene oxide.

I. Experimental Method:

1. Culture and activation: the EO-05 strain and the EO-degrading potential bacteria (i.e., the original strain before acclimation) were taken out from −80° C. refrigerator and 10 µL of each was inoculated in 100 mL tryptone soy broth (TSB) medium, respectively, and cultivate for 48 h (37° C., 200 rpm). The number of cells in the culture liquid is $10^{10}$-$10^{12}$ cfu/mL.

2. Nutrient broth liquid culture medium was made as follows: 10 g peptone and 5 g sodium chloride were added to 1000 mL of distilled water, divided into 400 mL portions, sterilized at 121° C. for 20 min, and cool to room temperature for storage. To make liquid medium containing no carbon source but 400 mg/L or 800 mg/L ethylene oxide, 160 mg or 320 mg of ethylene oxide, respectively, were injected to the medium with a closed syringe before use.

3. Comparative Test of Ethylene Oxide Degradation

To conduct a comparative experiment of ethylene oxide degradation, the following treatment and control groups were incubated in a 37° C. incubator for 48 hours.

Figure 4:
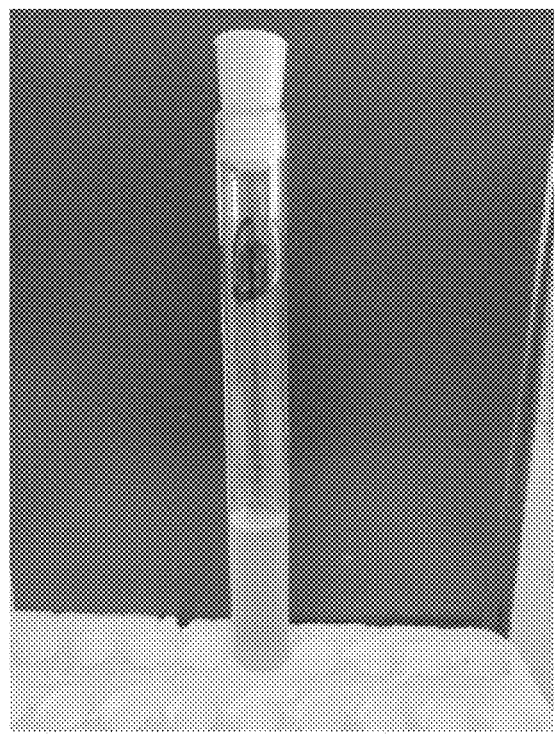
FIG. 4 shows a photo of bacterial colony growth of the EO-05 strain in a carbon-free medium with 800 mg/L of ethylene oxide at a constant temperature of 37° C. for 48 hours in the comparative EO degradation test according to Example 4, wherein the EO-05 strain was obtained by the inductive acclimation processes according to Example 3.

Treatment Group 1 (EO-05 strain/800 mg/L ethylene oxide): 5 mL of the bacterial culture of the pure cultured strain EO-05 obtained according to Example 3, with a live cell count of $10^{10}$-$10^{12}$ cfu/mL, was inoculated into 400 mL of nutrient broth liquid medium containing no carbon source but 800 mg/L ethylene oxide as the inducer, with a live bacteria cell count in the medium being $10^8$-$10^{10}$ cfu/mL. The cell culture result after 48 hours is shown in FIG. 4.

Figure 5:
FIG. 5 shows a photo of bacterial colony growth of the EO-degrading potential bacteria (i.e., the original strain before acclimation) in a carbon-free medium with 800 mg/L of ethylene oxide at a constant temperature of 37° C. for 48 hours in the comparative EO degradation test according to Example 4, wherein the EO-degrading potential bacteria was obtained according to Example 1.

Treatment Group 2 (original strain before acclimation/800 mg/L ethylene oxide): 5 mL of the bacterial culture of the EO-degrading potential bacteria (i.e., the original strain before acclimation) obtained according to Example 1, with a live cell count of $10^{10}$-$10^{12}$ cfu/mL, was inoculated into 400 mL of nutrient broth liquid medium containing no carbon source but 800 mg/L ethylene oxide as the inducer, with a live bacteria cell count in the medium being $10^8$-$10^{10}$ cfu/mL. The cell culture result after 48 hours is shown in FIG. 5.

Control group 1 (No inoculation/800 mg/L ethylene oxide): Nutrient broth liquid medium containing no carbon source but 800 mg/L ethylene oxide without inoculation of the EO-05 strain or EO-degrading potential bacteria.

Treatment Group 3 (EO-05 strain/400 mg/L ethylene oxide): 5 mL of the bacterial culture of the pure cultured strain EO-05 obtained according to Example 3, with a live cell count of $10^{10}$-$10^{12}$ cfu/mL, was inoculated into 400 mL of nutrient broth liquid medium containing no carbon source but 400 mg/L ethylene oxide as the inducer, with a live bacteria cell count in the medium being $10^8$-$10^{10}$ cfu/mL;

Treatment Group 4 (original strain before acclimation/400 mg/L ethylene oxide): 5 mL of the bacterial culture of the EO-degrading potential bacteria (i.e., the original strain before acclimation) obtained according to Example 1, with a live cell count of $10^{10}$-$10^{12}$ cfu/mL, was inoculated into 400 mL of nutrient broth liquid medium containing no carbon source but 400 mg/L ethylene oxide as the inducer, with a live bacteria cell count in the medium being $10^8$-$10^{10}$ cfu/mL; and Control Group 2 (No inoculation/400 mg/L ethylene oxide): Nutrient broth liquid medium containing no carbon source but 400 mg/L ethylene oxide without inoculation of the EO-05 strain or EO-degrading potential bacteria.

4. Gas Chromatography (GC) Analysis

To calculate the concentrations of residual ethylene oxide and the degradation rates, samples were taken from the above Treatment groups 1-4 and Control groups 1-2 after the comparative test and sent to the Shaanxi Provincial Center for Disease Control and Prevention for gas chromatography analysis according to the methods described in "Sanitary Standards for Disposable Hygiene Products" (GB15979-2002) of China National Standards as follows:

- a series of ethylene oxide standards of 0-200 mg/L concentrations were made by taking a certain volume of pure ethylene oxide gas with a sealed syringe for dissolving in deionized water;
- the subject samples to be analyzed were prepared by diluting samples from the treatment and control groups 5 times with deionized water;
- after the GC instrument with hydrogen flame ionization detector (FID) is stabilized and under the same conditions, 2 μL each of the ethylene oxide standards and the diluted samples to be analyzed were injected into the GC instrument, wherein each sample was measured twice in parallel;
- qualitive determination was conducted according to the retention time and quantitative calculation on each peak area was performed to take the average value;
- an ethylene oxide standard curve was plotted according to the measurement data of the ethylene oxide standards, and the concentrations of residual ethylene oxide within each sample from the control and treatment groups were found based on the peak area corresponding to ethylene oxide thereof; and
- the degradation rate of ethylene oxide for each sample was calculated according to the following formula: Degradation Rate (%)=(Control Group Concentration−Treatment Group Concentration)/Control Group Concentration×100; specifically, the degradation rates of Treatment groups 1 and 2 were calculated based on Control Group 1, while those of Treatment groups 3 and 4 calculated based on Control Group 2.

Additionally, the percentage of increase in the ethylene oxide degradation ability of the strain before and after acclimation was calculated according to the following formula:

Percentage of increase in degradation ability (%)=(Degradation Rate (%) of the strain after acclimation−Degradation Rate (%) of the strain before acclimation)/Degradation Rate (%) of the strain before acclimation).

Other details of the experiment include Column: Chromosorb 101HP60-80 mesh, glass column 2 m long, diameter 3 mm Column temperature: 120° C. Detector: 150° C., Gasifier: 150° C.; Carrier gas volume: Nitrogen: 35 ml/min, Hydrogen: 35 ml/min, Air: 350 ml/min, and the pre-column pressure is about 108 Kpaa.

II. Experimental Results

The experimental results are summarized in Table 2 below. As shown in Table 2, the EO-05 strain was capable of degrading ethylene oxide with concentrations as high as 400 mg/L and 800 mg/L with no carbon source, while the degradation rates were greatly improved compared to the original strain without acclimation. Specifically, the degradation rate of EO-05 strain of 400 mg/L ethylene oxide was as high as 92.90%, which was 350.97% higher than that of the original strain without acclimation. For 800 mg/L ethylene oxide, the EO-05 strain demonstrated a degradation rate of 68.65% and an increase of 585.12% compared to the original strain without acclimation.

TABLE 2

Comparative ethylene oxide degradation experiment (no carbon source) of *Alcaligenes faecalis* EO-05 strain and the original *Alcaligenes faecalis* strain before acclimation

| Test Group | Test strain | EO concentration before test (mg/L) | EO concentration after test (mg/L) | Degradation Rate (%) |
|---|---|---|---|---|
| Treatment Group 1 | EO-05 strain | 800 | 160.5 | 68.65% |
| Treatment Group 2 | Original strain | 800 | 460.6 | 10.02% |
| Control Group 1 | N/A | 800 | 511.9 | / |
| Treatment Group 3 | EO-05 strain | 400 | 16.4 | 92.90% |
| Treatment Group 4 | Original strain | 400 | 183.5 | 20.60% |
| Control Group 2 | N/A | 400 | 231.1 | / |

Comparative tests may be carried out in other samples containing ethylene oxide, such as sewage, sludge, exhaust gas, or wastewater, such as industrial (including industries related to petroleum and derivative products), medical treatment (such as ethylene oxide sterilant) and other sewage, sludge, exhaust gas, or wastewater.

An *Alcaligenes faecalis* strain of the invention comprising the 16S rDNA sequence of SEQ ID NO: 4 can also be used in comparative tests.

Example 5

Treatment of Ethylene Oxide Sterilization Waste Gas

In general, ethylene oxide sterilization waste gas can be absorbed into water. The water containing the absorbed ethylene oxide can be contacted with an *Alcaligenes faecalis* strain of the present invention in a method of biodegrading ethylene oxide. The water containing the absorbed ethylene oxide can be discharged or transferred to an anaerobic vessel, such as an anaerobic sewage tank. An *Alcaligenes faecalis* strain of the present invention can then be added to the tank, thereby biodegrading the ethylene oxide.

In particular, (1) after the ethylene oxide sterilizer has sterilized, the ethylene oxide sterilization exhaust gas generated is fed into a hydration system, which uses the internal circulating water to absorb the incoming ethylene oxide sterilization exhaust gas, and several cycles of absorption produce ethylene oxide wastewater containing about 243.15 mg/L of ethylene oxide.

(2) The ethylene oxide wastewater with the concentration of about 243.15 mg/L of ethylene oxide was passed into an aerobic bio-ethylene oxide treatment cell inoculated with the EO-05 strain, the strain concentration was $10^{10}$-$10^{12}$ cfu/mL, the inoculation amount was 1%-2%, the EO-05 strain used the active sludge in the aerobic bio-ethylene oxide treatment cell as the culture, ethylene oxide was used as the carbon source and energy for metabolism, growth and proliferation, thus achieving the purpose of ethylene oxide treatment.

The mixture in the treatment cell was continuously stirred, the temperature was controlled at 32° C.-42° C. and the treatment was for 48 hours. The results showed that the residual concentration of ethylene oxide in the treated wastewater was 20.96 mg/L with a treatment efficiency of 91.38%.

The above concentrations were detected by gas chromatography in accordance with GB 15979-2002 (Appendix D), which is explained above. The degradation rate was calculated according to the following formula: Degradation rate= (starting concentration−residual concentration)/starting concentration.

As another practical application, activated sludge can be contacted with an *Alcaligenes faecalis* strain of the present invention, thereby biodegrading ethylene oxide in the activated sludge.

In the above-described tests and applications, the degradation rate is at least 10%, 15%, 20%, 25%, 30%, 35%, 40%, 50%, 60%, 70%, 75%, 80%, 90%, 95%, 100%, 125%, 150%, 200%, or 500% greater relative to the degradation rate of ethylene oxide in the absence of the *Alcaligenes faecalis* strain EO-05 or *Alcaligenes faecalis* strain comprising the 16S rDNA sequence of SEQ ID NO: 4.

The detailed embodiments described herein are only for the purpose of illustrating the present disclosure, and are not intended to limit the scope of the present disclosure in any way. It would be understood by a person skilled in the art that various changes and modifications can be made to the embodiments described herein without departing from the scope and spirit of the present disclosure. Such changes and modifications are contemplated by the present disclosure, the scope of which should only be defined by the following claims.

What is claimed is:

1. A product which is a biologically pure culture of *Alcaligenes faecalis* strain EO-05 with the Deposit Number of CGMCC No. 18435 capable of biodegrading ethylene oxide at a higher rate than a naturally occurring *Alcaligenes faecalis*.

2. The product according to claim 1, wherein the product is prepared by culturing the *Alcaligenes faecalis* strain EO-05.

3. The product according to claim 1, wherein the *Alcaligenes faecalis* strain EO-05 has a concentration of at least $10^8$ cfu/mL.

4. A method for biodegrading ethylene oxide or decreasing the amount of ethylene oxide in a material comprising adding to the material comprising ethylene oxide an amount of the product of claim 1.

5. The method according to claim 4, wherein the method has a degradation rate of at least 10% greater relative to the degradation rate of ethylene oxide in the absence of the product.

6. The method according to claim 4, wherein the material comprising ethylene oxide comprises sewage or wastewater.

7. The method according to claim 6, wherein the wastewater is selected from the group consisting of wastewater from a petrochemical process and wastewater from a medical process.

8. A method for biodegrading ethylene oxide or decreasing the amount of ethylene oxide in material, wherein the method comprises:
inoculating the product of claim 1 into tryptone soy broth culture medium for 24-48 hours of incubation at 37° C. using a shaker at 200 rpm to obtain an *Alcaligenes faecalis* EO-05 culture; and
adding to the material comprising ethylene oxide an amount of the *Alcaligenes faecalis* EO-05 culture.

9. The method according to claim 4, wherein the product is capable of using ethylene oxide as a carbon source and is capable of growing normally with ethylene oxide as the main carbon source in the culture.

* * * * *